(12) United States Patent
Noble et al.

(10) Patent No.: US 8,148,511 B2
(45) Date of Patent: Apr. 3, 2012

(54) **METHODS AND COMPOSITIONS FOR THE DETECTION AND QUANTIFICATION OF *E. COLI* AND *ENTEROCOCCUS***

(75) Inventors: Rachel T. Noble, Beaufort, NC (US); Angelia D. Blackwood, Newport, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 158 days.

(21) Appl. No.: 11/859,032

(22) Filed: Sep. 21, 2007

(65) Prior Publication Data
US 2008/0233572 A1  Sep. 25, 2008

Related U.S. Application Data

(60) Provisional application No. 60/847,715, filed on Sep. 28, 2006.

(51) Int. Cl.
*C07H 21/04* (2006.01)
*C12Q 1/68* (2006.01)
*C12P 19/34* (2006.01)
(52) U.S. Cl. ............... 536/24.3; 435/6.12; 435/91.2
(58) Field of Classification Search .................. None
See application file for complete search history.

(56) References Cited

U.S. PATENT DOCUMENTS

| | | | |
|---|---|---|---|
| 6,001,564 A | 12/1999 | Bergeron et al. | |
| 6,326,145 B1 | 12/2001 | Whitcombe et al. | |
| 6,387,652 B1 | 5/2002 | Haugland et al. | |
| 6,583,275 B1 * | 6/2003 | Doucette-Stamm et al. | 536/23.1 |
| 2004/0180328 A1 * | 9/2004 | Ecker et al. | 435/5 |
| 2005/0059064 A1 * | 3/2005 | Obst et al. | 435/6 |

OTHER PUBLICATIONS

Ram et al. Sequence-based source tracking of *Escherichia coli* based on genetic diversity of beta-glucuronidase. J. Environ. Quality (2004) vol. 33, pp. 1024-1032.*
Buck et al. Design strategies and performance of custom DNA sequencing primers. BioTechniques (1999) vol. 27, No. 3, pp. 528-536).*
GenBank Accession No. AR348384, representing SEQ ID No. 2995 from U.S. Patent No. 6,583,275. Doucette-Stamm et al. (Aug. 2003).*
GenBank Accession No. AY447077, representing partial sequence of *E. coli* beta-glucuronidase gene. Ram et al. (Nov. 2003).*
Behr, T., et al., "A Nested Array of rRNA Targeted Probes for the Detection and Identification of *Enterococci* by Reverse Hybridization," *System. Appl. Microbiol.*, 2000, pp. 563-572, vol. 23.
Betzl, D., et al., "Identification of *Lactococci* and *Enterococci* by Colony Hybridization with 23S rRNA-Targeted Oligonucleotide Probes,"*Appl. Environ. Microbiol.*, Sep. 1990, pp. 2927-2929, vol. 56, No. 9.
Fuhrman, J.A., et al., "Rapid Detection of Enteroviruses in Small Volumes of Natural Waters by Real-Time Quantitative Reverse Transcriptase PCR,"*Appl. Environ. Microbiol.*, Aug. 2005, pp. 4523-4530, vol. 71, No. 8.
Haughland, R.A., et al., "Comparison of *Enterococcus* Measurements in Freshwater at Two Recreational Beaches by Quantitative Polymerase Chain Reaction and Membrane Filter Culture Analysis," *Water Research*, 2005, pp. 559-568, vol. 39.
Whitcombe, D., et al., "Detection of PCR Products Using Self-probing Amplicons and Fluorescence," *Nat. Biotechnol.*, Aug. 1999, pp. 804-807, vol. 17.

* cited by examiner

*Primary Examiner* — Kenneth R. Horlick
*Assistant Examiner* — David Thomas
(74) *Attorney, Agent, or Firm* — Alston & Bird LLP

(57) ABSTRACT

The present invention is drawn to methods and compositions for the rapid assessment of fecal indicator bacteria in a sample. Provided herein are novel primer and probe compositions for use in detecting the presence of these organisms in a sample, particularly using quantitative PCR methods. Provided herein are novel oligonucleotide primers and probes, including the primers set forth in SEQ ID NO:1-4, the novel oligonucleotide probe sequences set forth in SEQ ID NO:5-8, and methods for using these primers and probes for the detection and/or quantification of fecal indicator bacteria, particularly *E. coli* and *Enterococcus* spp. in a sample.

18 Claims, 4 Drawing Sheets

METHODS AND COMPOSITIONS FOR THE DETECTION AND QUANTIFICATION OF *E. COLI* AND *ENTEROCOCCUS*

CROSS REFERENCE TO RELATED APPLICATION

This application claims the benefit of U.S. Provisional Application Ser. No. 60/847,715, filed Sep. 28, 2006, the content of which is herein incorporated by reference in its entirety.

REFERENCE TO SEQUENCE LISTING SUBMITTED ELECTRONICALLY

The official copy of the sequence listing is submitted electronically via EFS-Web as an ASCII formatted sequence listing with a file named "333589_SequenceListing.txt", created on Sep. 19, 2007, and having a size of 2.0 kilobytes and is filed concurrently with the specification. The sequence listing contained in this ASCII formatted document is part of the specification and is herein incorporated by reference in its entirety.

FIELD OF THE INVENTION

This invention provides compositions and methods for the detection and/or quantification of indicator bacterium, particularly *Escherischia coli* and *Enterococcus* spp., in a sample.

BACKGROUND OF THE INVENTION

Epidemiology studies have shown that recreational exposure from swimming or surfing in locations impacted by contaminated storm water leads to a significant increase in a variety of illnesses (Griffin, 2003, supra; Haile et al. (1999) *Epidemiology* 10:355-363). There can be even greater potential exposure through the consumption of contaminated shellfish due to concentration of contaminants by the filter feeders (Gerba (1988) Food Technol. 42:99-103; Griffin, 2003, supra; Pina et al. (1998) *Appl. Environ. Microbiol.* 64:3376-3382; Schwab et al. (1998) *J. Food Prot.* 61:1674-1680). The illnesses of concern include (but are not limited to) diarrhea, ocular and respiratory infection, gastroenteritis, hepatitis, myocarditis, meningitis, paralysis, and severe chronic disease.

In the United States, *Escherichia coli* and enterococci are currently used as indicators of microbial water quality, serving as proxies for the potential presence of pathogenic bacteria and viruses.

Previous health and epidemiological studies by the US Environmental Protection Agency (US EPA) have demonstrated that colony-forming unit (CFU) densities of the bacterial genus *Enterococcus* in both marine and freshwater samples are directly correlated with gastroenteritis illness rates in swimmers exposed to these waters (Cabelli et al. (1982) *J. Epidemiol.* 115:606-616; Dufour (1984) EPA-600/1-84-004, Office of Research and Development, US Environmental Protection Agency, Cincinnati, Ohio). The strains commonly called *E. coli* can cause different infections in man or in animals according to the provision with pathogenic genes (urinary infections, choleriform or hemorrhagic diarrhea, dysentery syndrome, hemolytic and uremic syndrome, septicemia, neonatal meningitis, various purulent infections). Based on these data, guidance has been issued on the maximum concentrations of these organisms that may be associated with acceptable health risks (Dufour and Ballantine (1986) EPA 440/5-84-002, Washington D.C.). Since then an improved, selective culture method has been developed for measuring *Enterococcus* concentrations in recreational water samples have shown that changes in water quality conditions during this delay period can frequently lead to notifications to the public that are not fully protective of swimmer health (Messer and Dufour (1998) *Appl. Environ. Microbiol.* 64:678-680; US EPA (2002) EPA 821/R-02/022, 2002, US Environmental Protection Agency, Office of Water (4303T), Washington D.C.). However, this method still requires at least 24 hours to obtain results.

Increasing interest is now being directed towards the possible use of molecular microbial analysis methods with shorter reporting times. One such technology is the quantitative polymerase chain reaction (QPCR). Primer sets and probes associated with this technology have now been developed for the specific detection of a number of different fecal indicator organisms and waterborne pathogens (Ludwig and Schleifer (2000) *Syst. Appl. Microbiol.* 23:556-562; Lyon (2001) *Appl. Environ. Microbiol.* 67:4685-4693; Brinkman et al. (2003) *Appl. Environ. Microbiol.* 69:1775-1782; Foulds et al. (2002) *J. Appl. Microbiol.* 93:825-834; Blackstone et al. (2003) *J. Microbiol. Methods* 53:149-155; Frahm and Obst (2003) *J. Microbiol. Methods* 52:123-131; Guy et al. (2003) *Appl. Environ. Microbiol.* 69:5178-5185; Noble et al. (2003) *J. Water Health* 1: 195-207). The availability of portable instrumentation that can be operated at or near the site and the development of rapid methods for processing samples for QPCR analysis (Brinkman et al. 2003, supra) have reduced the potential overall time requirements of this method to a matter of only a few hours, from sampling to results.

Several patents disclose methods to detect harmful bacteria. U.S. Pat. No. 6,207,818, U.S. Pat. No. 6,060,252, U.S. Pat. No. 6,054,269 and U.S. Pat. No. 5,298,392 all describe the amplification and detection of such harmful bacteria.

There is a vital need for rapid methods to quantify indicator bacteria in biological, industrial, and environmental samples that yield equivalent results to existing methods. Additional methods are needed to rapidly detect the presence of harmful bacteria in biological, industrial, and environmental samples.

SUMMARY OF THE INVENTION

The present invention is drawn to methods and compositions for the rapid assessment of fecal indicator bacteria in a sample, particularly from biological, industrial, and environmental sources. Provided herein are novel primer and probe compositions for use in detecting the presence of these organisms in a sample, particularly using quantitative PCR methods.

In one embodiment, the present invention provides novel oligonucleotide primers and probe sets. These primers and probe sets can be used in amplification methods (such as PCR, particularly quantitative PCR) and packaged into kits for use in amplification methods for the purpose of detecting fecal indicator bacteria in a test sample, particularly a biological, industrial, or environmental sample. Additionally, these primers and/or probe sets can be used in amplification methods (such as polymerase chain reaction) to evaluate or monitor the efficacy of treatments being used to eliminate fecal indicator bacteria from a biological, industrial, or environmental source.

Thus, in one embodiment, the present invention provides for novel oligonucleotide primers set forth in SEQ ID NO:1, 2 and 3, and the novel oligonucleotide probe sequences set forth in SEQ ID NO:5-8. In another embodiment, the present invention provide a novel probe comprising, in the 5' to 3' direction, one of a fluorophore or a quencher, an oligonucleotide comprising SEQ ID NO:5 or 7, the other of the fluorophore or the quencher, a PCR blocker moiety, and an oligonucleotide comprising SEQ ID NO:1. This composition can be used in combination with SEQ ID NO:2 in a method of detecting fecal indicator bacteria, particularly *Escherichia coli*, in a sample. In another embodiment, the present invention provide a novel probe comprising, in the 5' to 3' direction, one of a fluorophore or a quencher, an oligonucleotide comprising SEQ ID NO:6 or 8, the other of the fluorophore or the quencher, a PCR blocker moiety, and an oligonucleotide comprising SEQ ID NO:3. This composition can be used in combination with SEQ ID NO:4 in a method of detecting fecal indicator bacteria, particularly *Enterococcus* spp., in a sample.

Further provided are kits useful for the detection and/or quantification of fecal indicator bacteria in a sample comprising a composition according to the present invention. The kits may further comprise instructions for using the provided composition in a polymerase-based amplification reaction, e.g., PCR or QPCR.

In another embodiment, the present invention relates to a method of detecting a fecal indicator bacterium in a sample using polymerase-based amplification of a target nucleic acid region present in the bacteria, the method comprising: (a) providing a test sample suspected of containing fecal indicator bacteria, (b) contacting the sample with a composition of the invention under conditions sufficient to provide polymerase-based nucleic acid amplification products comprising the target nucleic acid region; and (c) detecting the presence of the nucleic acid amplification products as an indication of the presence of live fecal indicator bacteria in the test sample.

The present invention also relates to use of the primers according to the present invention, wherein the primers or probes have the sequences according to any of the sequences as defined in SEQ ID NO:1-8.

DETAILED DESCRIPTION

Overview

Figure 1:
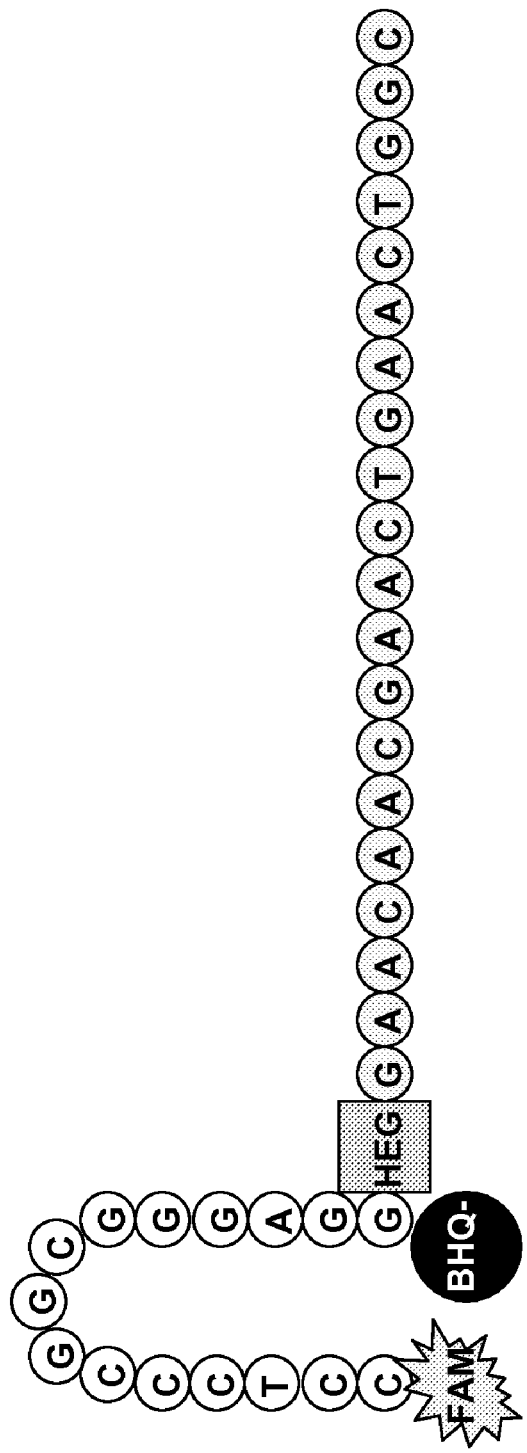
FIG. 1 is a schematic drawing of the SCORPIONS® probe for *E. coli* in the quenched configuration. The structure is as follows, from 5' to 3': a fluorophore (FAM), SEQ ID NO:7, a quencher (the black hole quencher-1 (BHQ-1)), hexethylene glycol (HEG), and SEQ ID NO:1.

The methods and compositions of the present invention are directed at the detection and/or quantification of fecal indicator bacteria, particularly *Enterococcus* spp. and *E. coli*, in a sample by amplification of the target genes encoding 23S rRNA and b-glucuronidase, respectively, using a polymerase-based amplification method, particularly polymerase chain reaction. As used herein, "polymerase chain reaction" or "PCR" refers to an in vitro method for amplifying a specific polynucleotide template sequence (or "target nucleic acid"). "Fecal indicator bacteria" refers to the microorganisms present in a sample source that are associated with (or "indicate") the presence of fecal matter in that sample. For the purposes of the present invention, the fecal indicator bacteria are *E. coli* and *Enterococcus* spp.

In one embodiment, one or more oligonucleotide primer sequence(s) is covalently attached to one or more oligonucleotide probe sequence(s). The probe is flanked by a fluorophore on one end of the oligonucleotide probe and a quencher on the opposite end (or within) the oligonucleotide probe. This primer/probe complex further comprises PCR blocker molecules between the primer and the probe sequence to prevent the incorporation of the probe sequence into the primer extension product. The oligonucleotide probe is designed to have two stems at each end that are complementary to each other so that it will be in a stem-loop (or "hairpin") secondary structure when it is not yet hybridized to the primers' extension product. In this embodiment, the fluorophore and quencher that are attached to the 5' and 3' ends of the probe are in close proximity when the probe is free in solution and no fluorescence will be detectable. When the probe unfolds as it binds to the extended primer (i.e., "primer extension product"), the fluorophore and quencher are separated and fluorescence can be detected in order to quantify the amount of amplification product. This fluorescence corresponds to the amount of target nucleic acid present in the sample.

In another embodiment, the primer/probe complex comprises the oligonucleotide primer set forth in SEQ ID NO:1 covalently attached to a probe comprising SEQ ID NO:5 or 7. This complex further comprises a fluorophore and a quencher flanking the probe sequence, and at least one PCR blocker molecule (e.g., hexethylene glycol) between the primer and the probe. This primer/probe complex can be used with the oligonucleotide primer set forth in SEQ ID NO:2 to rapidly detect the presence of *E. coli* in a sample using quantitative polymerase chain reaction (QPCR).

In yet another embodiment, the primer/probe complex comprises the oligonucleotide primer set forth in SEQ ID NO:3 covalently attached to a probe set comprising SEQ ID NO:6 or 8. This complex further comprises a fluorophore and a quencher flanking the probe sequence, and at least one PCR blocker molecule (e.g., hexethylene glycol) between the primer and the probe. This primer/probe complex can be used with the oligonucleotide primer set forth in SEQ ID NO:4 to rapidly detect the presence of *Enterococcus* spp. in a sample using quantitative polymerase chain reaction (QPCR). Each of these primer/probe complexes can be used alone or in combination to quantitate the amount of fecal indicator bacteria present in a test sample.

Sample Source

The methods and compositions of the present invention are useful in the detection and/or quantification of fecal indicator bacteria in biological, industrial, or environmental samples. In one aspect of the invention, the environmental sample is derived from recreational water. "Recreational water" includes ocean water, pond water, lake water, creek water, river water, swimming pools, hot tubs, saunas, and the like. The invention is equally suited for use in other sample sources, including but not limited to, shellfish or other aquatic organisms, terrestrial organisms, groundwater, leachate, wastewater, sewer water, blackwater, graywater, bilge water, ballast water, feed water, process water, industrial water, irrigation water, rain water, runoff water, cooling water, non-potable water, potable water, drinking water, semi-pure water, and/or spent ultra-pure water, etc.

Extraction of nucleic acid material from a sample can be conducted using routine techniques known in the art. "Nucleic acid extracted from bacteria" is understood as meaning either the total nucleic acid, or the ribosomal RNA or the genomic DNA, or even the nucleic acid obtained from the reverse transcription of nucleic acid from bacteria.

Nucleic acid material is extracted using standard methods, e.g., the glass bead milling and glass milk adsorption method or any similar procedure of extracting nucleic acid material. Additionally, commercially available kits can be employed in the present methods, for example, the Fecal DNA Extraction Kit or the Soil DNA Extraction Kit (MO BIO Laboratories, Inc., Carlsbad, Calif.) using the manufacturers instructions or the protocols provided in the Experimental Examples section below.

Oligonucleotide Primers

In one embodiment of the present invention, oligonucleotide primers are provided for use in the detection and/or quantification of fecal indicator bacteria in a sample. As used herein, a "primer" refers to a type of oligonucleotide having or containing a sequence complementary to a target polynucleotide present in or derived from the indicator bacterium, which hybridizes to the target polynucleotide through base pairing. In one embodiment, the primers of the invention are those comprising the nucleotide sequences set forth in SEQ ID NO:1-4. The term "oligonucleotide" refers to a short polynucleotide, typically less than or equal to 150 nucleotides long (e.g., between 5 and 150, preferably between 10 to 100, more preferably between 15 to 50 nucleotides in length). However, as used herein, the term is also intended to encompass longer or shorter polynucleotide chains.

As used herein, the terms "target polynucleotide" and "target nucleic acid" refer to a polynucleotide whose amount is to be determined in a sample. In the present invention, the target nucleic acid corresponds to the nucleic acid that encodes beta-glucuronidase (for *E. coli*) or 23S rRNA (for *Enterococcus* spp.). A "target nucleic acid" of the present invention contains a known sequence of at least 20 nucleotides, preferably at least 50 nucleotides, more preferably at least 100 or more nucleotides, for example, 500 or more nucleotides. A "target nucleic acid" of the invention may be a naturally occurring polynucleotide (i.e., one existing in nature without human intervention), or a recombinant polynucleotide (i.e., one existing only with human intervention), including but not limited to genomic DNA, cDNA, plasmid DNA, total RNA, mRNA, tRNA, rRNA. The target polynucleotide also includes amplified products of itself, for example, as in a polymerase chain reaction. According to the invention, a "target polynucleotide" or "target nucleic acid" may contain a modified nucleotide which include phosphorothioate, phosphite, ring atom modified derivatives, and the like.

As used herein, the term "complementary" refers to the concept of sequence complementarity between regions of two polynucleotide strands or between two regions of the same polynucleotide strand. A first region of a polynucleotide is complementary to a second region of the same or a different polynucleotide if, when the two regions are arranged in an antiparallel fashion, at least one nucleotide of the first region is capable of base pairing with a base of the second region. Therefore, it is not required for two complementary polynucleotides to base pair at every nucleotide position. "Complementary" refers to a first polynucleotide that is 100% or "fully" complementary to a second polynucleotide and thus forms a base pair at every nucleotide position. "Complementary" also refers to a first polynucleotide that is not 100% complementary (e.g., 90%, or 80% or 70% complementary) and contains mismatched nucleotides at one or more nucleotide positions. Thus, the oligonucleotides of the present invention are capable of detecting species of *Escherichia* or *Enterococcus* that differ in the target nucleic acid region that is complementary to the polynucleotides disclosed herein as SEQ ID NO:1, 2, 3, 4, 5, 6, 7, or 8.

As used herein, the term "hybridization" is used in reference to the pairing of complementary (including partially complementary) polynucleotide strands. Hybridization and the strength of hybridization (i.e., the strength of the association between polynucleotide strands) is impacted by many factors well known in the art including the degree of complementarity between the polynucleotides, stringency of the conditions involved affected by such conditions as the concentration of salts, the melting temperature (Tm) of the formed hybrid, the presence of other components (e.g., the presence or absence of polyethylene glycol), the molarity of the hybridizing strands and the G:C content of the polynucleotide strands.

The primers of the present invention can be prepared using techniques known in the art, including, but not limited to, cloning and digestion of the appropriate sequences and direct chemical synthesis.

Chemical synthesis methods that can be used to make the primers of the present invention, include, but are not limited to, the phosphotriester method described by Narang et al., Methods in Enzymology, 68:90 (1979), the phosphodiester method disclosed by Brown et al., Methods in Enzymology, 68:109 (1979), the diethylphosphoramidate method disclosed by Beaucage et al., Tetrahedron Letters, 22:1859 (1981) and the solid support method described in U.S. Pat. No. 4,458,066. The use of an automated oligonucleotide synthesizer to prepare synthetic oligonucleotide primers of the present invention is also contemplated herein. Additionally, if desired, the primers can be labeled using techniques known in the art and described below.

Oligonucleotide Probes

One or more of the oligonucleotide primers of the present invention may further comprise one or more probe sequences. The probes may be separate from the oligonucleotide primers ("bimolecular probes"), or, preferably, attached to the oligonucleotide primer ("unimolecular probes" or "tailed probes"). See, for example, the self-probing sequences (e.g., SCORPIONS™ primers, also referred to as "tailed probes") described in Whitcombe et al. (1999) *Nature Biotechnol.* 17:804-807 and U.S. Pat. No. 6,326,145, both of which are herein incorporated by reference in their entirety.

As used herein, the term "probe" refers to a polynucleotide that forms a hybrid structure with a primer extension product due to complementarity of at least one sequence in the probe with a sequence in the primer extension product. By "primer extension product" is intended the nucleic acid product that results from polymerase-based extension (using the target nucleic acid as a template) of the oligonucleotide primer comprising the sequences disclosed herein as SEQ ID NO:1-4. The polynucleotide regions of the probe can be composed of DNA and/or RNA and/or synthetic nucleotide analogs.

Preferably, the probe does not contain a sequence complementary to the oligonucleotide primer sequence(s) described above. The probe of the present invention is ideally less than or equal to 100 nucleotides in length, for example less than or equal to 80, 70, 60, 50, 40, 30, 20, or less than 10 nucleotides in length.

In some embodiments, the probe according to the present invention comprises a hairpin sequence. A "hairpin sequence" or a "stem loop sequence," as used herein, comprises two self-complementary sequences that may form a double-stranded stem region, separated by a loop sequence. The two regions of the oligonucleotide which comprise the double-stranded stem region are substantially complementary to each other, resulting in self-hybridization under the appropriate conditions. However, the stem can include one or more mismatches, insertions or deletions, so long as the hairpin structure is retained under the appropriate conditions (e.g., temperature) for hybridization of the stem region. The hairpin sequence can additionally comprise single-stranded region(s) that extend from the double-stranded stem segment. In a unimolecular (or "tailed") probe, the hairpin sequence is located at the 5' end of the oligonucleotide primer sequence, optionally separated by a linker sequence and/or other moieties as described below. The stem region of the hairpin can be between 2 to 20 base pairs, typically between 3 to 10 base pairs or between 3 and 8 base pairs.

In one embodiment, the sequence of the stem of the hairpin structure is designed such that hybridization to target nucleic acid is avoided. Therefore, the sequence of the stem of the hairpin sequence shares no homology with the target nucleic acid. In addition, the stem structure is designed such that hybridization to regions of the probe outside of the stem forming regions is avoided. Therefore, the sequence of the stem regions shares no homology to other parts of the probe (i.e., no homology to the loop sequence).

In another embodiment, at least part of the sequence of the stem of the hairpin structure is complementary to the primer extension product and thus is capable of hybridizing thereto. Preferably, self-hybridization of the stem is designed to be thermodynamically favored over the binding of probe to mismatch target sequence. The stability and melting temperature of hairpin sequences can be determined, for example, using programs such as mfold (Zuker (1989) *Science* 244:48-52) or Oligo 5.0 (Rychlik & Rhoads (1989) *Nucleic Acids Res.* 17:8543-51).

As used herein, "Tm" and "melting temperature" are interchangeable terms which are the temperature at which 50% of a population of double-stranded polynucleotide molecules becomes dissociated into single strands. The equation for calculating the Tm of polynucleotides is well known in the art. For example, the Tm may be calculated by the following equation: $Tm = 69.3 + 0.41 \times (G+C)\% - 650/L$, wherein L is the length of the probe in nucleotides. The Tm of a hybrid polynucleotide may also be estimated using a formula adopted from hybridization assays in 1 M salt, and commonly used for calculating Tm for PCR primers: [(number of A+T)× 2° C. +(number of G+C)×4° C.], see, for example, Newton et al. (1997) *PCR* 2nd Ed. (Springer-Verlag, New York). Other more sophisticated computations exist in the art, which take structural as well as sequence characteristics into account for the calculation of Tm. A calculated Tm is merely an estimate; the optimum temperature is commonly determined empirically.

The single-stranded loop sequence intervening the two stem-forming regions can vary in length between 1 to 40 bases, typically 2 to 30 bases, 3 to 20 bases, 4 to 15 bases, or 4 to 10 bases. In one embodiment, the sequence of the loop hybridizes to a portion of the primer extension product resulting from polymerase-based extension of the primer sequences of the invention (e.g., SEQ ID NO:1-4). In a further embodiment, the sequence of the loop comprises SEQ ID NO:5 or 6. In yet a further embodiment, the sequence of the loop comprises SEQ ID NO:7 or 8.

Linker Sequences

The probe according to the present invention can further comprise a linker sequence, placed between the hairpin sequence and the oligonucleotide primer sequence. A linker can be useful, for example, to ensure that the hairpin sequence forms without interfering with the target binding sequence hybridizing to the target nucleic acid, or to allow attachment of labels without interfering with hybridization of the target binding sequence to the target nucleic acid. As used herein, the "target binding sequence" corresponds to the primer sequences disclosed as SEQ ID NO:1-4.

The linker sequence can comprise between 1 and 40 bases, typically between 1 and 25, between 1 and 20, between 1 and 15, between 1 and 10 and between 1 and 5 bases. There is no strict requirement regarding the linker sequence, so long as the linker sequence does not interfere with the formation of hairpin loop structure, does not hybridize to undesirable target, or does not interfere with hybridization of the probe sequence to the primer extension product.

The probe may further comprise a blocking moiety which prevents polymerase mediated chain extension of the target binding sequence. In one embodiment of the present invention, the PCR blocker is hexethylene glycol (HEG) inserted at the 5' end of the oligonucleotide primer sequence, between the probe and the primer. Other suitable blocker moieties include 2-O-alkyl RNA, peptide nucleic acid, or nucleotide sequences which will prevent the extension of the primer template. This embodiment is further described in European Patent No. 0 416 817 and U.S. Pat. No. 5,525,494, the contents of which are incorporated herein by reference in their entirety.

Labeling

The primers and/or probes of the present invention can further include one or more labels to facilitate monitoring of amplification reactions. As used herein, the term "label" or "labeled" refers to any atom or moiety which can be used to provide a detectable (preferably, quantifiable) signal, and which can be attached to a polynucleotide, oligonucleotide primer or probe. A wide variety of labels and conjugation techniques, including direct and indirect labeling, are known and are reported extensively in both the scientific and patent literature. Examples of labels that can be used include radionucleotides, enzymes, substrates, cofactors, inhibitors, fluorescent moieties, intercalators, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241.

Fluorophore

In one embodiment, the primers and/or probes can be labeled with a fluorophore and a quencher in such a manner that the fluorescence emitted by the fluorophore in intact probes (e.g., in the stem-loop configuration (unimolecular) or bound to an oligonucleotide comprising a quencher described below (bimolecular), but not bound to primer extension product) is substantially quenched, whereas the fluorescence in probes that are not intact are not quenched, resulting in an increase in overall fluorescence upon denaturation of the stem region and hybridization of at least a portion of the probe to the primer extension product. Furthermore, the generation of a fluorescent signal during real-time detection of the amplification products allows accurate quantitation of the initial number of target sequences in a sample.

A wide variety of fluorophores can be used, including but not limited to: 5-FAM (also called 5-carboxyfluorescein; also called Spiro(isobenzofuran-1(3H), 9'-(9H)xanthene)-5-carboxylic acid, 3',6'-dihydroxy-3-oxo-6-carboxyfluorescein); 5-Hexachloro-Fluorescein ([4,7,2',4',5',7'-hexachloro-(3',6'-dipivaloyl-fluoresceinyl)-6-carboxylic acid]); 6-Hexachloro-Fluorescein ([4,7,2',4',5',7'-hexachloro-(3',6'-dipivaloylfluoresceinyl)-5-carboxylic acid]); 5-Tetrachloro-Fluorescein ([4,7,2',7'-tetrachloro-(3',6'-dipivaloylfluoresceinyl)-5-carboxylic acid]); 6-Tetrachloro-Fluorescein ([4,7,2',7'-tetrachloro-(3',6'-dipivaloylfluoresceinyl)-6-carboxylic acid]); 5-TAMRA (5-carboxytetramethylrhodamine; Xanthylium, 9-(2,4-dicarboxyphenyl)-3,6-bis(dimethylamino); 6-TAMRA (6-carboxytetramethylrhodamine; Xanthylium, 9-(2,5-dicarboxyphenyl)-3,6-bis(dimethylamino); EDANS (5-((2-aminoethyl)amino)naphthalene-1-sulfonic acid); 1,5-IAEDANS (5-((((2-iodoacetyl)amino)ethyl)amino)naphthalene-1-sulfonic acid); DABCYL (4-((4-(dimethylamino) phenyl)azo)benzoic acid) Cy5 (Indodicarbocyanine-5) Cy3 (Indo-dicarbocyanine-3); and BODIPY FL (2,6-dibromo-4, 4-difluoro-5,7-dimethyl-4-bora-3a,4a-diaza-s-indacene-3-proprionic acid), Rox, as well as suitable derivatives thereof.

Quencher

As used herein, the term "quencher" refers to a chromophoric molecule or part of a compound, which is capable of reducing the emission from a fluorescent donor when attached to or in proximity to the donor. Quenching may occur by any of several mechanisms including fluorescence resonance energy transfer (FET), photoinduced electron transfer, paramagnetic enhancement of intersystem crossing, Dexter exchange coupling, and exciton coupling such as the formation of dark complexes. Therefore, the quencher can be any material that can quench at least one fluorescence emission from an excited fluorophore being used in the assay. There is a great deal of practical guidance available in the literature for selecting appropriate reporter-quencher pairs for particular probes, as exemplified by the following references: Clegg (1993) *Proc. Natl. Acad. Sci. USA* 90:2994-2998; Wu et al. (1994) *Anal. Biochem.* 218:1-13; Pesce et al., editors (1971) *Fluorescence Spectroscopy* (Marcel Dekker, New York); White et al. (1970) *Fluorescence Analysis: A Practical Approach* (Marcel Dekker, New York); and the like. The literature also includes references providing exhaustive lists of fluorescent and chromogenic molecules and their relevant optical properties for choosing reporter-quencher pairs, e.g., Berlman (1971) *Handbook of Fluorescence Spectra of Aromatic Molecules,* 2nd Edition (Academic Press, New York); Griffiths (1976) *Colour and Constitution of Organic Molecules* (Academic Press, New York); Bishop, editor (1972) *Indicators* (Pergamon Press, Oxford); Haugland (1992) *Handbook of Fluorescent Probes and Research Chemicals* (Molecular Probes, Eugene, Oreg.); Pringsheim (1949) *Fluorescence and Phosphorescence* (Interscience Publishers, New York), all of which incorporated herein by reference in their entirety. Further, there is extensive guidance in the literature for derivatizing reporter and quencher molecules for covalent attachment via common reactive groups that can be added to an oligonucleotide, as exemplified by the following references, see, for example, Hauglans, 1992, supra; Ullman et al., U.S. Pat. No. 3,996,345; Khanna et al., U.S. Pat. No. 4,351,760, all of which herein incorporated by reference.

A number of commercially available quenchers are known in the art, and include but are not limited to DABCYL, BHQ-1, BHQ-2, and BHQ-3 (Biosearch Technologies, Inc., Novato, Calif.).

Attachment of Fluorophore and Quencher

The probe according to the present invention has one of the fluorophore or quencher attached to the 3' nucleotide of the probe sequence. Attachment of the fluorophore or quencher is preferably at the hydroxyl moiety of the 3' terminal nucleotide. Attachment can be made via direct coupling, or alternatively using a linker sequence or other suitable molecule of between 1 and 5 atoms in length.

For the internal attachment of the fluorophore or quencher, linkage can be made using any of the means known in the art. Appropriate linking methodologies for attachment of many dyes to oligonucleotides are described in many references, e.g., Marshall (1975) *Histochemical J.* 7:299-303; Menchen et al., U.S. Pat. No. 5,188,934; Menchen et al., European Patent Application 87310256.0; and Bergot et al., International Application PCT/US90/05565. All are herein incorporated by reference.

The other of the fluorophore or quencher can be attached anywhere within the probe outside the hairpin sequence, preferably at a distance from the other of the fluorophore/ quencher such that sufficient amount of quenching occurs when the oligonucleotide probe is intact. For example, if the fluorophore is attached to the 3' nucleotide of the primer/ probe complex, the quencher can be attached within the probe within either the target binding sequence or the optional linker sequence. In one embodiment, the fluorophore and quencher are placed between 5 and 40 nucleotides of each other. In another embodiment, the fluorophore and quencher are placed between 10 and 34, between 15 and 30, or between 20 to 25 nucleotides of each other.

In another embodiment, the primer/probe complex does not comprise a quencher sequence. In this example, the probe does not assume a hairpin configuration but is linear ("open" format). A quencher is attached to a separate oligonucleotide that is complementary to (and is capable of hybridizing to) at least a portion of the probe sequence, wherein the complementary portion is adjacent to the fluorophore or at least in sufficient proximity such that the fluorescence emitted by the fluorophore is absorbed by the quencher when the two oligonucleotides hybridize. In this embodiment, the probe is designed such that hybridization of the probe to primer extension product is thermodynamically favored over reannealing of the probe to the complementary oligonucleotide comprising the quencher sequence. This type of probe is herein referred to as a "bimolecular" probe.

Attachment of Probes to a Solid Support

The probes of the present invention may also be linked to a solid support either directly, or through a chemical spacer. A solid support useful according to the invention includes but is not limited to silica-based matrices, cellulosic materials, plastic materials, membrane-based matrices and beads comprising surfaces including, but not limited to styrene, latex or silica based materials and other polymers. Magnetic beads are also useful according to the invention. Solid supports can be obtained commercially from several manufacturers.

It is well known by those with skill in the art that oligonucleotides can be synthesized with certain chemical and/or capture moieties, such that they can be coupled to solid supports. Examples of attaching oligonucleotides to solid supports can be found, for example, in U.S. Patent Application No. U.S. 2003/0165912 A1, which is herein incorporated by reference in its entirety. Suitable capture moieties include, but are not limited to, biotin, a hapten, a protein, a nucleotide sequence, an antigenic moiety, or a chemically reactive moiety. Such oligonucleotides may either be used first in solution and then captured onto a solid support, or first attached to a solid support and then used in a detection reaction.

As discussed supra, in a preferred embodiment, the probe oligonucleotides are structured such that fluorescence energy transfer does not occur between the fluorophore and quencher of the labeled oligonucleotide probe upon fluorophore excitation when the labeled oligonucleotide probe is hybridized to the primer extension product. Examples of these types of probe structures include: SCORPIONS™ probes (as described in Whitcombe et al., 1999, supra and U.S. Pat. No. 6,326,145, Sunrise probes (as described in Nazarenko et al. (1997) Nuc. Acids Res. 25:2516-2521; U.S. Pat. No. 6,117,635, the disclosure of which is herein incorporated by reference), Molecular Beacons (Tyagi et al. (1996) Nature Biotechnology 14:303-308; U.S. Pat. No. 5,989,823, the disclosure of which is incorporated herein by reference), and conformationally assisted probes (as described in U.S. Provisional Patent Application Ser. No. 60/138,376, the disclosure of which is herein incorporated by reference). In these embodiments, the probe comprises a hybridization domain complementary to a sequence of the primer extension product.

Thus, in a preferred embodiment of the present invention, the compositions comprise, in the 5' to 3' direction, a fluorophore, a probe sequence comprising SEQ ID NO:5 or 7, a quencher, HEG, and an oligonucleotide primer comprising SEQ ID NO:1. This primer/probe complex (also referred to herein as a "SCORPIONS® probe" or "tailed probe") is useful in the detection and/or quantification of *E. coli* in a sample, particularly when used in a PCR or QPCR reaction that further comprises an oligonucleotide primer comprising SEQ ID NO:2. In another embodiment, the compositions comprise, in the 5' to 3' direction, a fluorophore, a probe sequence comprising SEQ ID NO:6 or 8, a quencher, HEG, and an oligonucleotide primer comprising SEQ ID NO:3. This primer/probe complex is useful in the detection and/or quantification of *Enterococcus* spp. in a sample, particularly when used in a PCR or QPCR based reaction that further comprises the oligonucleotide primer set forth in SEQ ID NO:4.

As is understood in the art, the oligonucleotide primers and/or probes set forth in SEQ ID NO:1-6 may further comprise additional sequences or moieties to facilitate hybridization to the target nucleic acid or primer extension product, to facilitate attachment of a quencher, fluorophore, blocker or other suitable moiety, or to facilitate the formation of a desired secondary structure (e.g., stem loop). Thus, in various embodiments, the oligonucleotide probe comprising SEQ ID NO:5 is set forth in SEQ ID NO:7, and the oligonucleotide probe comprising SEQ ID NO:6 is set forth in SEQ ID NO:8.

It is further understood that variants and fragments of the oligonucleotide primer and/or probe sequences disclosed herein can be used in the methods of the invention. For example, the sequences can be shorter or longer than the sequences disclosed herein as SEQ ID NO:1-8, or may have 1 to 5, or 5 to 10, nucleotide substitutions so long as the oligonucleotide primers retain the ability to hybridize to the target nucleic acid in such a manner as to initiate (under the appropriate conditions as described elsewhere herein) the template-dependent extension of the primer sequence in a PCR or equivalent reaction, and so long as the probe retains the ability to hybridize to the primer extension product under the appropriate conditions.

Further, because signals are strong and the priming function is identical to the primers that do not comprise the preferred SCORPIONS® structure described above, not all of the primer used in the methods of the present invention (e.g., QPCR) needs to be in the SCORPIONS® configuration. In some embodiments, the primers used in the methods of the present invention comprise less than 100%, less than 90%, less than 80%, 70%, 60%, 50%, 40%, 30%, or less than 20% of primers in the SCORPIONS® configuration. The remaining primers in the reaction can be labeled according to the procedures provided herein or known in the art, or can be unlabeled. The SCORPIONS® can be added before the start of the amplification reaction, or can be added at a time subsequent to the start of the amplification reaction. Preferably, the SCORPIONS® are added at the start of the reaction.

Polymerase-Based Amplification

Numerous different PCR or QPCR protocols are known in the art and exemplified herein below and can be directly applied or adapted for use using the presently-described compositions for the detection and/or quantification of fecal indicator bacteria in a sample. Generally, in PCR, a target polynucleotide sequence is amplified by reaction with at least one oligonucleotide primer or pair of oligonucleotide primers. The primer(s) hybridize to a complementary region of the target nucleic acid and a DNA polymerase extends the primer(s) to amplify the target sequence. Under conditions sufficient to provide polymerase-based nucleic acid amplification products, a nucleic acid fragment of one size dominates the reaction products (the target polynucleotide sequence which is the amplification product). The amplification cycle is repeated to increase the concentration of the single target polynucleotide sequence. The reaction can be performed in any thermocycler commonly used for PCR. However, preferred are cyclers with real-time fluorescence measurement capabilities, for example, SMARTCYCLER® (Cepheid, Sunnyvale, Calif.), ABI PRISM 7700® (Applied Biosystems, Foster City, Calif.), ROTOR-GENE™ (Corbett Research, Sydney, Australia), LIGHTCYCLER® (Roche Diagnostics Corp, Indianapolis, Ind.), ICYCLER® (Biorad Laboratories, Hercules, Calif.) and MX4000® (Stratagene, La Jolla, Calif.).

Quantitative PCR (QPCR) (also referred as real-time PCR) is preferred under some circumstances because it provides not only a quantitative measurement, but also reduced time and contamination. As used herein, "quantitative PCR (or "real time QPCR") refers to the direct monitoring of the progress of a PCR amplification as it is occurring without the need for repeated sampling of the reaction products. In quantitative PCR, the reaction products may be monitored via a signaling mechanism (e.g., fluorescence) as they are generated and are tracked after the signal rises above a background level but before the reaction reaches a plateau. The number of cycles required to achieve a detectable or "threshold" level of fluorescence varies directly with the concentration of amplifiable targets at the beginning of the PCR process, enabling a measure of signal intensity to provide a measure of the amount of target nucleic acid in a sample in real time.

In a preferred embodiment, a labeled probe is used to detect the extension product generated by PCR amplification. Any probe format utilizing a labeled probe comprising the sequences of the invention may be used, e.g., such as SCORPIONS™ probes, sunrise probes, TAQMAN® probes, or molecular beacon probes as is known in the art or described elsewhere herein.

PCR Conditions

Methods for setting up a PCR reaction are well known to those skilled in the art. The reaction mixture minimally comprises template nucleic acid (except in the case of a negative control as described below) and oligonucleotide primers and/ or probes in combination with suitable buffers, salts, and the like, and an appropriate concentration of a nucleic acid polymerase. As used herein, "nucleic acid polymerase" refers to an enzyme that catalyzes the polymerization of nucleoside triphosphates. Generally, the enzyme will initiate synthesis at the 3'-end of the primer annealed to the target sequence, and will proceed in the 5'-direction along the template until synthesis terminates. An appropriate concentration includes one which catalyzes this reaction in the presently described methods. Known DNA polymerases include, for example, *E. coli* DNA polymerase I, T7 DNA polymerase, *Thermus thermophilus* (Tth) DNA polymerase, *Bacillus stearothermophilus* DNA polymerase, *Thermococcus litoralis* DNA polymerase, *Thermus aquaticus* (Taq) DNA polymerase and *Pyrococcus furiosus* (Pfu) DNA polymerase.

In addition to the above components, the reaction mixture produced in the subject methods includes primers, probes and deoxyribonucleoside triphosphates (dNTPs). The SCORPIONS® primer/probe complex is present at about 10 to about 1500 nM, or about 50 to about 1200 nM, or about 100 to about 1000 nM, or about 250 nM. The reverse primer is present at about 10 to about 500 nM, or about 25 to about 400 nM, or about 50 to about 300 nM, or about 250 nM.

Usually the reaction mixture will further comprise four different types of dNTPs corresponding to the four-naturally occurring nucleoside bases, i.e. dATP, dTTP, dCTP and dGTP. In the subject methods, each dNTP will typically be present in an amount ranging from about 10 to 5000 μM, usually from about 20 to 1000 μM, about 100 to 800 μM, or about 300 to 600 μM.

The reaction mixture prepared in the first step of the subject methods further includes an aqueous buffer medium that includes a source of monovalent ions, a source of divalent cations and a buffering agent. Any convenient source of monovalent ions, such as potassium chloride, potassium acetate, ammonium acetate, potassium glutamate, ammonium chloride, ammonium sulfate, and the like may be employed. The divalent cation may be magnesium, manganese, zinc and the like, where the cation will typically be magnesium. Any convenient source of magnesium cation may be employed, including magnesium chloride, magnesium acetate, and the like. The amount of magnesium present in the buffer may range from 0.5 to 10 mM, but will preferably range from about 1 to about 6 mM, or about 3 to about 5 mM. Representative buffering agents or salts that may be present in the buffer include Tris, Tricine, HEPES, MOPS and the like, where the amount of buffering agent will typically range from about 5 to 150 mM, usually from about 10 to 100 mM, and more usually from about 20 to 50 mM, where in certain preferred embodiments the buffering agent will be present in an amount sufficient to provide a pH ranging from about 6.0 to 9.5, or about pH 8.0. Other agents which may be present in the buffer medium include chelating agents, such as EDTA, EGTA and the like.

In preparing the reaction mixture, the various constituent components may be combined in any convenient order. For example, the buffer may be combined with primer, polymerase and then template nucleic acid, or all of the various constituent components may be combined at the same time to produce the reaction mixture.

Alternatively, commercially available premixed reagents can be utilized in the methods of the invention according to the manufacturer's instructions, or modified to improve reaction conditions (e.g., modification of buffer concentration, cation concentration, or dNTP concentration, as necessary), including, for example, TAQMAN® Universal PCR Master Mix (Applied Biosystems), OMNIMIX® or SMARTMIX® (Cepheid), IQ™ Supermix (Bio-Rad Laboratories), LIGHTCYCLER® FastStart (Roche Applied Science, Indianapolis, Ind.), or BRILLIANT® QPCR Master Mix (Stratagene, La Jolla, Calif.).

Following preparation of the reaction mixture, the reaction mixture is subjected to primer extension reaction conditions ("conditions sufficient to provide polymerase-based nucleic acid amplification products"), i.e., conditions that permit for polymerase mediated primer extension by addition of nucleotides to the end of the primer molecule using the template strand as a template. In many embodiments, the primer extension reaction conditions are amplification conditions, which conditions include a plurality of reaction cycles, where each reaction cycle comprises: (1) a denaturation step, (2) an annealing step, and (3) a polymerization step. The number of reaction cycles will vary depending on the application being performed, but will usually be at least 15, more usually at least 20 and may be as high as 60 or higher, where the number of different cycles will typically range from about 20 to 40. For methods where more than about 25, usually more than about 30 cycles are performed, it may be convenient or desirable to introduce additional polymerase into the reaction mixture such that conditions suitable for enzymatic primer extension are maintained.

The denaturation step comprises heating the reaction mixture to an elevated temperature and maintaining the mixture at the elevated temperature for a period of time sufficient for any double stranded or hybridized nucleic acid present in the reaction mixture to dissociate. For denaturation, the temperature of the reaction mixture will usually be raised to, and maintained at, a temperature ranging from about 85 to 100, usually from about 90 to 98° C. and more usually from about 93 to 96° C., for a period of time ranging from about 3 to 120 sec, usually from about 5 to 30 sec.

Following denaturation, the reaction mixture will be subjected to conditions sufficient for primer annealing to template nucleic acid present in the mixture (if present), and for polymerization of nucleotides to the primer ends in a manner such that the primer is extended in a 5' to 3' direction using the nucleic acid to which it is hybridized as a template, i.e., conditions sufficient for enzymatic production of primer extension product. The temperature to which the reaction mixture is lowered to achieve these conditions will usually be chosen to provide optimal efficiency and specificity, and will generally range from about 50 to 75, usually from about 55 to 70 and more usually from about 60 to 68° C., more particularly around 62° C. Annealing conditions will be maintained for a period of time ranging from about 15 sec to 30 min, usually from about 20 sec to 5 min, or about 30 sec to 1 minute, or about 43 seconds.

This step can optionally comprise one of each of an annealing step and an extension step with variation and optimization of the temperature and length of time for each step. In a 2-step annealing and extension, the annealing step is allowed to proceed as above. Following annealing of primer to template nucleic acid, the reaction mixture will be further subjected to conditions sufficient to provide for polymerization of nucleotides to the primer ends as above. To achieve polymerization conditions, the temperature of the reaction mixture will typically be raised to or maintained at a temperature ranging from about 65 to 75, usually from about 67 to 73° C. and maintained for a period of time ranging from about 15 sec to 20 min, usually from about 30 sec to 5 min.

The above cycles of denaturation, annealing and polymerization may be performed using an automated device, typically known as a thermal cycler. Thermal cyclers that may be employed are described elsewhere herein as well as in U.S.

Pat. Nos. 5,612,473; 5,602,756; 5,538,871; and 5,475,610, the disclosures of which are herein incorporated by reference.

The methods of the invention can also be used in non-PCR based applications to detect a target nucleic acid sequence, where such target that may be immobilized on a solid support. Methods of immobilizing a nucleic acid sequence on a solid support are known in the art and are described in Ausubel et al. *Current Protocols in Molecular Biology*, John Wiley and Sons, Inc. and in protocols provided by the manufacturers, e.g. for membranes: Pall Corporation, Schleicher & Schuell, for magnetic beads: Dynal, for culture plates: Costar, Nalgenunc, and for other supports useful according to the invention, CPG, Inc.

The person skilled in the art of nucleic acid amplification knows the existence of other rapid amplification procedures such as ligase chain reaction (LCR), transcription-based amplification systems (TAS), self-sustained sequence replication (3SR), nucleic acid sequence-based amplification (NASBA), strand displacement amplification (SDA) and branched DNA (bDNA) (Persing et al., 1993. Diagnostic Molecular Microbiology: Principles and Applications, American Society for Microbiology, Washington, D.C.). The scope of this invention is not limited to the use of amplification by PCR, but rather includes the use of any rapid nucleic acid amplification methods or any other procedures which may be useful with the sequences of the invention for the detection and/or quantification of fecal indicator bacteria.

Further, variations on the exact amounts of the various reagents and on the conditions for the PCR or other suitable amplification procedure (e.g., buffer conditions, cycling times, etc.) that lead to similar amplification or detection/quantification results are known to those of skill in the art and are considered to be equivalents. In one embodiment, the subject QPCR detection has a sensitivity of detecting fewer than 50 copies (preferably fewer than 25 copies, more preferably fewer than 15 copies, still more preferably fewer than 10 copies) of target nucleic acid (e.g., genomic or cDNA) in a sample. In one embodiment, a hot-start PCR reaction is performed (e.g., using a hot start Taq DNA polymerase) so as to improve PCR reaction by decreasing background from non-specific amplification and to increase amplification of the desired extension product.

Controls

The PCR or QPCR reaction of the present invention may contain various controls. Such controls should include a "no template" negative control, in which primers, buffer, enzyme(s) and other necessary reagents (e.g., magnesium chloride, nucleotides) are cycled in the absence of added test sample. A positive control including a known target nucleic acid should also be run in parallel. Both positive control and negative control may be included in the amplification reaction. A single reaction may contain either a positive control, a negative control, or a sample template, or a single reaction may contain both a sample template and a positive control.

In addition to "no template" controls, negative controls can also include amplification reactions with non-specific target nucleic acid included in the reaction, or can be samples prepared using any or all steps of the sample preparation (from nucleic acid extraction to amplification preparation) without the addition of a test sample (e.g., each step uses either no test sample or a purified water sample known to be free of indicator bacterium), or with the addition of a test sample that contains a non-specific bacterium such as *Lactococcus*. *Lactococcus* can be used as a specimen processing control because they are very similar in nature to *Enterococcus*. The use of a processing control provides useful information regarding the efficiency of extraction procedures without interfering in the detection of the indicator bacterium.

Confirmation of Primer Extension Product

If fecal indicator bacteria are present in the test sample, a single amplification product results for each of the two bacterial species. For *E. coli*, this amplification product is about 100 to about 200 base pairs in length, preferably about 127 base pairs in the length, whose termini are defined by the oligonucleotide primer(s) of the present invention (e.g., SEQ ID NO:1 and 2). For *Enterococcus* spp., this amplification product is about 100 to about 200 base pairs in length, preferably about 145 base pairs in the length, whose termini are defined by the oligonucleotide primer(s) of the present invention (e.g., SEQ ID NO:3 and 4). Each of these polynucleotide sequences (i.e., the amplification product or primer extension product) then serves as a template for the next reaction.

If desired, the identity of the primer extension or amplification product can be confirmed using standard molecular techniques including (for example) a Southern blot assay. In a Southern blot assay, the amplification products are separated by electrophoresis, transferred to a membrane (i.e. nitrocellulose, nylon, etc.), reacted with an oligonucleotide probe or any portion of the nucleic acid sequence of interest. The probe is then modified to enable detection. The modification methods can be the incorporation of a radiolabeled nucleotide or any number of non-radioactive labels (such as biotin).

The oligonucleotide probe used in the Southern blot assay is derived from the nucleic acid sequence of *Enterococcus* or *E. coli* and hence is specific for nucleic acid from *Enterococcus* or *E. coli*. The probe used in the Southern blot assay can be prepared using routine, standard methods. For example, the probe can be isolated, cloned and restricted using routine techniques known in the art or can be made using the chemical synthesis methods described previously herein.

Alternatively, the amplification products can be detected using dot blot analysis. Dot blot analysis involves adhering an oligonucleotide probe (such as the one described previously) to a nitrocellulose or solid support such as, but not limited to, a bead (such as, but not limited to, polystyrene beads, magnetic beads or non-magnetic beads, etc), walls of a reaction tray, strips (such as, but not limited to nitrocellulose strips), test tube. The sample containing the labeled amplification product is added, reacted, washed to removed unbound sample, and a labeled, amplified product attached to the probe is visualized using routine techniques known in the art. A more stringent way to verify the primer extension product or amplification product is through direct sequencing using techniques well known in the art.

Signal Detection

The amount of target nucleic acid can be quantified, for example, according to an increase in detectable fluorescence emitted by a fluorophore (i.e., "signal"). An "increase in fluorescence," as used herein, refers to an increase in detectable fluorescence emitted by a fluorophore. An increase in fluorescence may result, for example, when the distance between a fluorophore and a quencher is increased, for example due to the spatial separation of the quencher from the fluorophore, such that the quenching is reduced.

The sample may be screened for an increase in fluorescence using any convenient means, e.g., a suitable fluorometer, such as a thermostable-cuvette or plate-reader fluorometer. Fluorescence is suitably monitored using a known fluorometer. The signals from these devices, for instance in the form of photo-multiplier voltages, are sent to a data processor board and converted into a spectrum associated with each, sample tube. Multiple tubes, for example 96 tubes, can be assessed at the same time. Data may be collected in this way at frequent intervals, for example once every 10 ms throughout the reaction, once per cycle, or once after each of the final cycles, such as after the last 5, 4, 3, or 2 cycles. By monitoring the fluorescence of the reactive molecule from the sample during each cycle, the progress of the amplification reaction can be monitored in various ways. For example, the data provided by melting peaks can be analyzed, for example by calculating the area under the melting peaks and this data plotted against the number of cycles. The data can also be analyzed according to the method described in Haugland, et al. (2005) *Water Research* 39:559-568, which is herein incorporated by reference in its entirety.

Screening the mixture for a change in fluorescence provides one or more assay results, depending on whether the sample is screened once at the end of the primer extension reaction, or multiple times, e.g., after each cycle, of an amplification reaction (e.g., as is done in real time PCR monitoring).

The data generated as described above can be interpreted in various ways. In its simplest form, an increase in fluorescence from the sample over the course of or at the end of the amplification reaction is indicative of the presence of the target sequence present, i.e., primer extension product present, suggestive of the fact that the amplification reaction has proceeded and therefore the target sequence was in fact present in the sample. Quantitation is also possible by monitoring the amplification reaction throughout the amplification process.

In this manner, a reaction mixture is readily screened for the presence of fecal indicator bacteria. The methods are suitable for detection and/or quantification of either indicator bacterium alone as well as multiplex analyses, in which two or more different oligonucleotide probes corresponding to *E. coli* and *Enterococcus* spp. are employed to screen for both species. In this embodiment, the type of signaling molecule (e.g., the fluorophor, or fluorophore/quencher combination) used with each primer/probe set would be readily distinguishable in a multiplex assay. A number of convenient fluorophore/quencher pairs are detailed in the literature (for example Glazer, et al. (1997) *Current Opinion in Biotechnology* 8:94-102) and in catalogues such as those from Molecular Probes and Applied Biosystems.

Kits

Also provided are kits for practicing the subject methods. The kits according to the present invention will comprise at least: (a) a labeled oligonucleotide, where the kit includes two or more distinguishable oligonucleotides, e.g., that hybridize to either *E. coli* or *Enterococcus* spp., or both; and (b) instructions for using the provided labeled oligonucleotide(s) in a high fidelity amplification, e.g., PCR, reaction. The kits may separately provide oligonucleotides corresponding to each of *E. coli* and *Enterococcus* spp., may provide oligonucleotides corresponding to both bacteria packaged together but in separate reaction components, or may provide oligonucleotides corresponding to both bacteria packaged in the same reaction components.

The subject kits may further comprise additional reagents which are required for or convenient and/or desirable to include in the reaction mixture prepared during the subject methods, where such reagents include: one or more polymerases; an aqueous buffer medium (either prepared or present in its constituent components, where one or more of the components may be premixed or all of the components may be separate), and the like.

The various reagent components of the kits may be present in separate containers, or may all be precombined into a reagent mixture for combination with template nucleic acid.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

EXPERIMENTAL EXAMPLES

Methods

Sample Collection

The samples are collected in 200 ml-1000 ml volumes in triple HCl (5% v/v) rinsed, polypropylene or equivalent containers. A smaller volume can be used if sample is turbid or expected to contain high concentrations of indicator bacteria. Acid should be removed prior to sample collection and the tube rinsed three times with sample water. The samples are transported on ice and processed within 4 hours. Alternatively, 100 ml samples can be taken in sterile, disposable bottles (such as IDEXX sample bottles) if desired.

Sample Processing

A 100 ml volume of thoroughly mixed water sample is passed through a filter unit containing a 47 mm, 0.45 µm pore size polycarbonate (PC) filter. The filter is then rinsed with a small volume (5-10 ml) of sterile water. The PC filter is promptly removed using flamed or autoclaved (or disposable) forceps and placed in 2 ml screw cap tube provided in the DNA extraction kit, which already contains beads (MO BIO Laboratories). Alternatively, the filter can be placed in a sterile 2 ml tube and processed according to the crude bead beating protocol described below, or can be stored for later batch analysis in a 1.5 ml microfuge tube at −80° C.

Nucleic Acid Extraction

In this protocol, *Lactococcus* is used as a specimen processing control (SPC) for assessing nucleic acid extraction efficiency. *Lactococcus* cells are used as a specimen processing control because they are very similar in nature to *Enterococcus*. The oligonucleotide primers and probes are designed to hybridize to the same target nucleic acid as the *Enterococcus* primer/probes, which should provide a good proxy as to how *Enterococcus* cells behave during nucleic acid extraction. While it is not necessary to use these cells to get a quantitative result with either the *E. coli* or *Enterococcus* assays, it does provide useful information on nucleic acid extraction efficiency. The amount of *Lactococcus* cells that are added at the initiation of nucleic acid extraction is dependent on the final extraction volume.

*Lactococcus* cells are grown overnight (12 hours) in a culture of BHIB (Brain Heart Infusion Broth) at 37° C. with or without aeration. *Lactococcus* cells should be enumerated with a hemocytometer, fluorescence microscopy, or similar method that will give an accurate cell count. Generally, an overnight culture will yield $1\times10^7$ cells/ml without aeration and $1\times10^9$ cells/ml with aeration. The cells are aliquoted into 100 µl volumes and frozen at −20° C. or −80° C. after noting the cell count. Cells can be stored for approximately 3 months at −20° C. and 6 months or longer at −80° C.

*Lactococcus* cells should be thawed on ice and added immediately prior to the nucleic acid extraction at a concentration that will yield a final concentration of 100,000 cells/extraction tube. The amount added is directly dependent on the final nucleic acid extraction volume.

DNA Extraction Using the Fecal DNA Extraction Kit or the Soil DNA Extraction Kit The Fecal DNA Extraction kit and the Soil DNA Extraction Kit (MO BIO Laboratories) provide the advantages of bead beating, silica matrix technology, and reaction concentration. Also included with the kit is a PCR inhibitor removal solution that makes it ideal for samples containing PCR inhibitors such as humic acids that are found in plant materials and soil and lipids found in fecal matter. To avoid overloading the silica column, less than approximately 20 μg of total DNA (which is less than the theoretical DNA concentration contained in 100 ml of sample given typical cell counts of 1e6 to 1e7 per ml and 4.4 fg of DNA per cell) is added to the column.

This protocol has been slightly modified from the manufacturer's instructions for the alternative protocol to obtain maximum yield. The Bead Solution (400 μl) is added to the beads in 2 ml screw cap tubes. Next, 100 ml of sample or buffer (negative control) is filtered through a 47 mm diameter, 0.4 μm polycarbonate filter. The filter is folded and placed completely in Bead Solution. Solution S1 (400 μl) is added and inverted once to mix and then 110 μl of Solution IRS is added. If Solution S1 is precipitated, the solution is heated to dissolve before use.

The tubes are placed in a bead beater or secured horizontally using a vortex adapter tube holder (MO BIO) for the vortex. Alternatively, the tubes can secured horizontally on a flat-bed vortex pad with tape. The tubes are vortexed at maximum speed for 10 minutes on the vortexer or bead beated for 1 minute. The tubes are centrifuged at 10,000×g for 30 seconds. A new tube containing 200 μl of Solution S2 is prepared for each sample. The S2 supernatant is transferred to the fresh tube, vortexed for 5 seconds, and incubated at 4° C. for 5 min or longer. The tubes are centrifuged again for 1 minute at 10,000×g.

An additional clean tube containing 900 μl of Solution S3 is prepared. The supernatant from the S2 tube is transferred to Solution S3, mixed gently by pipetting up and down several times, and then 700 μl of the solution is transferred to the spin column. The spin column is centrifuged at 10,000×g for 30 seconds and the flow through is discarded. The spin column is removed and the flow through is discarded. The spin column is replaced and the remaining volume of supernatant from the S3 tube is processed as above.

Solution S4 (300 μl) is added to the filter and centrifuged for 30 seconds at 10,000×g. The flow through is discarded as above and the spin column is centrifuged again for 1 minute. The spin filter is carefully placed in a fresh microcentrifuge tube and 50 μl of Solution S5 is pipetted directly on the center of the white filter membrane. The filter is allowed to stand for 1 minute and then centrifuged for 1 minute. The flow through containing the extracted nucleic acid is stored at −20° C. or analyzed using QPCR.

DNA Extraction Using Bead Beating (Method According to Haugland et al., 2005, Supra)

Approximately 0.3 g of Zirconia beads (BioSpec Products, Inc, Bartlesville, Okla.) or similar beads are added to a 2 ml screw cap microcentrifuge tube. The beads are autoclaved at 121° C., 15 psi for 15 minutes on a gravity cycle. The PC filter containing the sample is placed into the tube containing beads and 500 μl AE Buffer (QIAGEN Inc., Valencia, Calif.) is added. The tube is placed on a bead mill (BioSpec) and beat at maximum speed for 1 minute, or alternatively beat for 10 minutes using a vortex adapter (MO BIO Laboratories) as described above. The solution is centrifuged for 5 minutes at maximum speed to pellet cellular debris and beads. A volume of 125 μl of the supernatant is removed, placed in a clean microcentrifuge tube (DNase and RNase free) and spun for an additional 5 minutes at maximum speed. A volume of 100 μl of the supernatant is placed in a clean tube on ice for further processing. This protocol is a crude extraction and does not remove inhibitors of PCR or nucleases. Extracted samples do not tolerate freeze thawing, so it is best to keep them at 4° C. if reanalyzing again the following day.

Q-PCR Analysis

A reaction mixture is prepared comprising dNTPs, magnesium chloride (or suitable cation), reaction buffer, DNA polymerase, primers and/or probes, and the negative control(s), positive control(s), test sample(s), or standard samples (typically serially-diluted nucleic acid extract from a known bacterial species). The total reaction volume is adjusted to 25 μl using sterile water. The concentration of each of the reaction components can be determined empirically, but typically will comprise about 1.5 to about 6 mM magnesium chloride, about 10 mM of each dNTP, and about 20 to about 50 mM suitable buffer. Methods for optimizing and performing QPCR analyses are well known in the art and additional guidance is provided elsewhere herein. Further, premixed reagents can be conveniently obtained from a variety of commercial sources as described elsewhere herein. The cycling conditions are as follows: 1 cycle at 95° C. for 2 minutes (hot start) followed by 45 cycles of 95° C. for 5 sec and 62° C. for 43 sec. The fluorescence is measured during the 62° C. cycle.

Data Analysis

The results may be analyzed using the delta Ct method (see Haugland et al., 2005, supra) or by directly extrapolating from a standard curve generated according to known methods using the results from the serially-diluted standard nucleic acid samples.

Comparison of ENT and EC SCORPIONS® to Existing Methods

Figure 3:
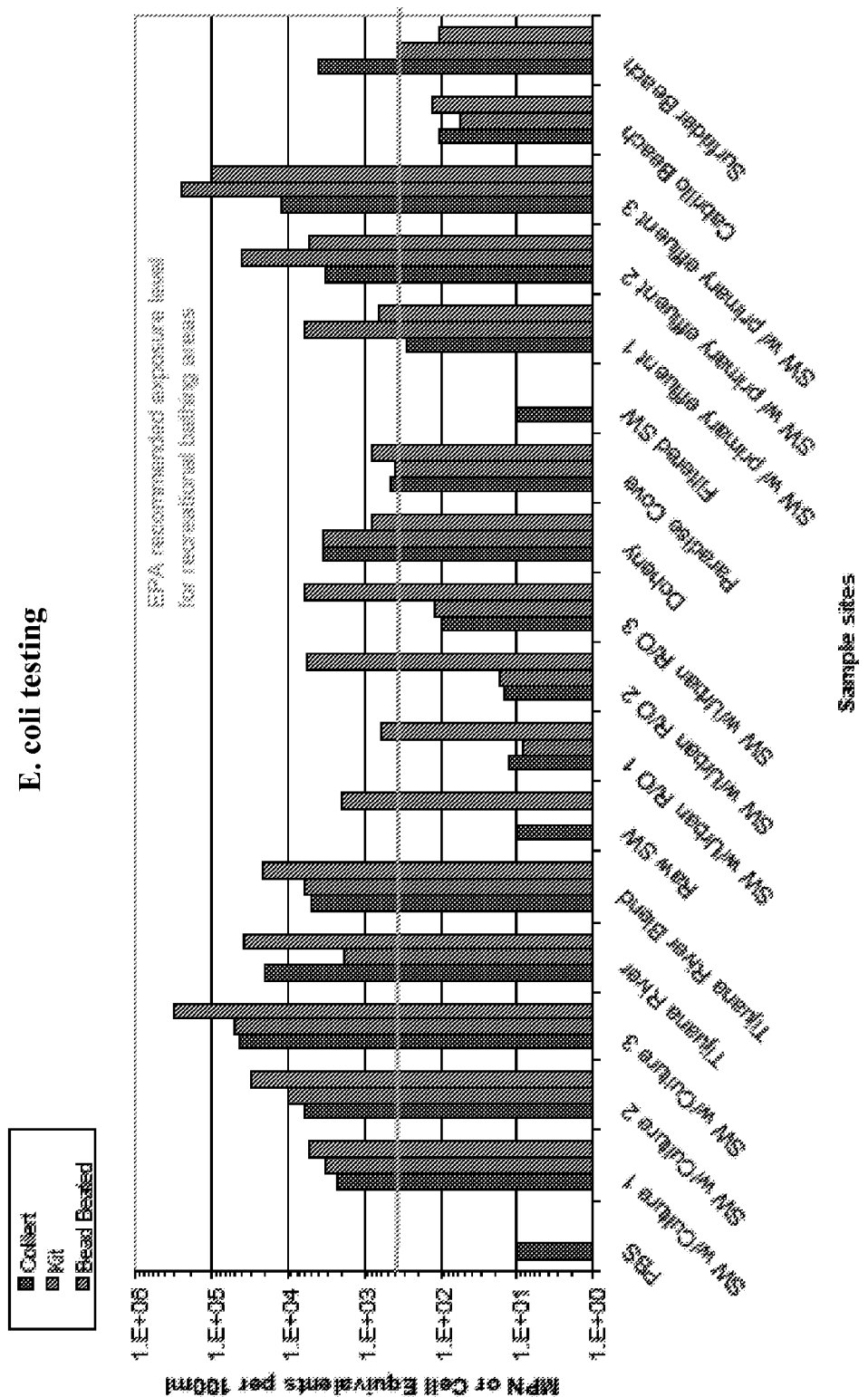
FIG. 3 demonstrates the efficacy of quantification of *E. coli* in water sources collected from various sites using the Colilert method ("Colilert") compared to QPCR using the EC SCORPIONS® probe and DNA that was extracted using a fecal DNA extraction kit ("kit"), or QPCR using the EC SCORPIONS® probe and DNA that was extracted using the bead beating method ("bead beated").
Figure 4:
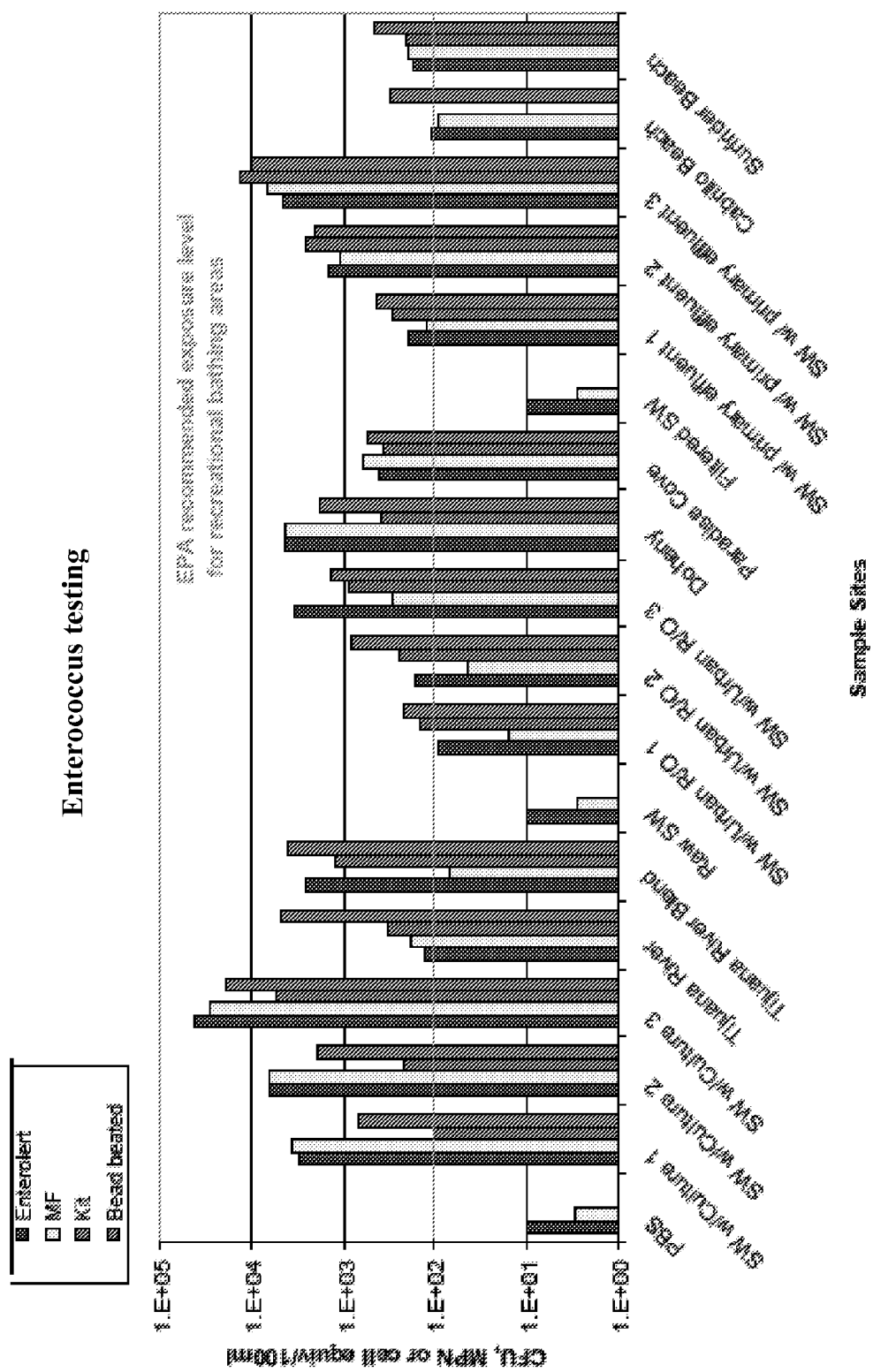
FIG. 4 demonstrates the efficacy of quantification of *Enterococcus* spp. in water sources collected from various sites using the ENTEROLERT™ method ("Enterolert") or the membrane filtration method ("MF") compared to QPCR using the ENT SCORPIONS® probe and DNA that was extracted using a fecal DNA extraction kit ("kit"), or QPCR using the ENT SCORPIONS® probe and DNA that was extracted using the bead beating method ("bead beated").

Samples were either collected from the southern California coastline or were made up in the lab. After transport to the lab, samples were split and processed for either *Enterococcus* or *E. coli*, using membrane filtration (EPA method 1600) or ENTEROLERT™, and COLILERT®-18, respectively (IDEXX, Westbrook, Me.). QPCR analysis was performed by filtration of 100 ml samples and either (1) bead beating (Haugland et al. 2005, supra), or (2) DNA extraction kit (ULTRACLEAN™ Soil DNA Extraction Kit, MO BIO) (FIGS. 3 and 4). For each QPCR analysis, enumeration of cell equivalents per 100 ml for each sample was performed using a standard curve approach. *Lactococcus* lactis was used as a specimen processing control (matrix control).

Figure 2:
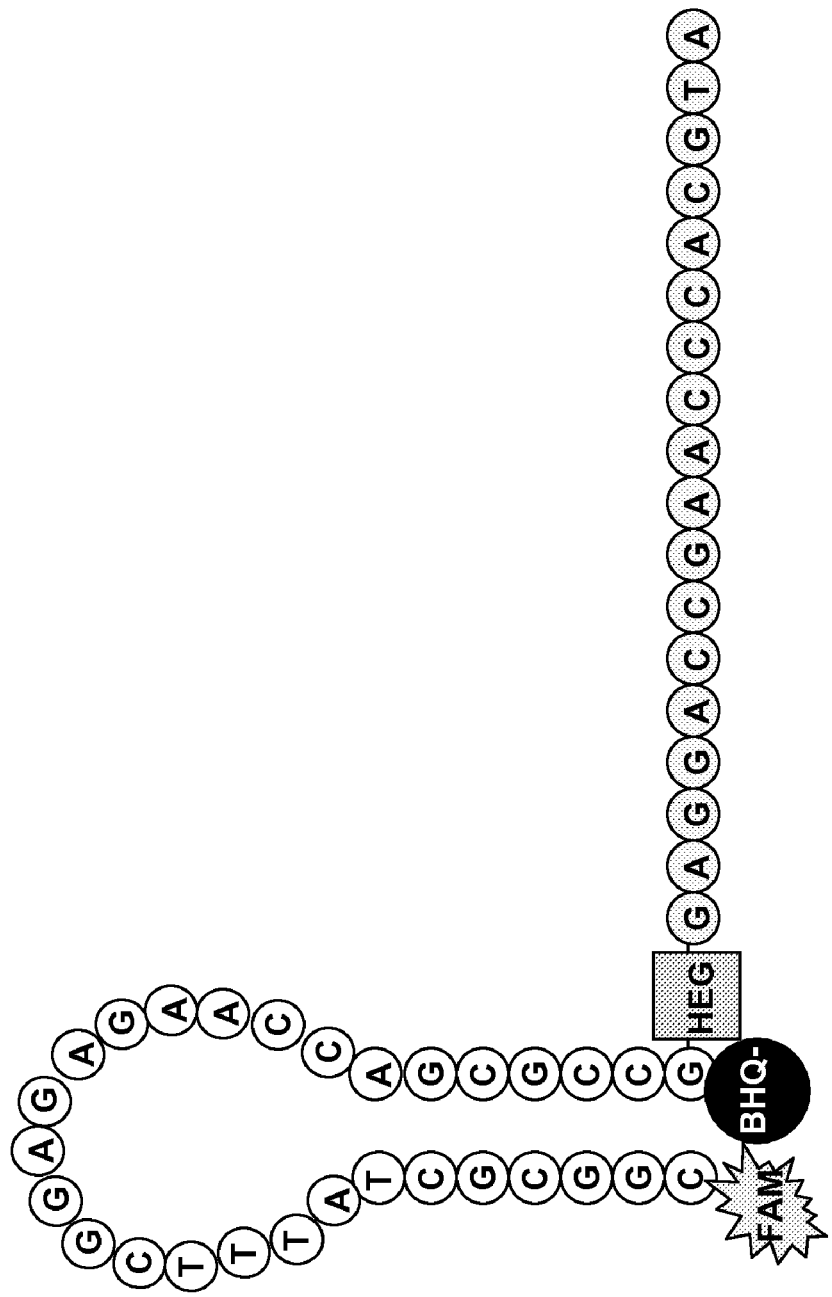
FIG. 2 is a schematic drawing of the SCORPIONS® probe for *Enterococcus* spp. in the quenched configuration. The structure is as follows, from 5' to 3': a fluorophore (FAM), SEQ ID NO:8, a quencher (the black hole quencher-1 (BHQ-1)), hexethylene glycol (HEG), and SEQ ID NO:3.

QPCR was performed as described above independently for EC and ENT using the EC SCORPIONS® probe (FIG. 1) and primer (SEQ ID NO:2), or the ENT SCORPIONS® probe (FIG. 2) and primer (SEQ ID NO:4). The conditions for the QPCR reaction were optimized according to Table 1.

TABLE 1

Optimization of QPCR conditions

| Parameter | Range Tested | Optimized |
|---|---|---|
| MgCl$_2$ | 4.0-6.0 mM | 4 mM* |
| Reverse Primer | 100-1000 nM | 250 nM |
| Primer/Probe Complex | 50-300 nM | 250 nM |
| dNTPs | 300-600 μM | 300 μM* |

*Optimization verifies that concentrations of MgCl$_2$ and dNTPs in OmniMix are optimal for reactions Results from QPCR assays (n=54) were directly compared to measurements conducted by 8 labs (using DEFINED SUBSTRATE TECHNOLOGY® (DST, or Colilert) or membrane filtration (MF) methods) to assess equivalency to existing methods and false-positive and -negative rates. For ENT QPCR, there was a strong correlation of the QPCR method to MF and DST (r2=0.89 and 0.87, respectively), and 82% threshold-based agreement (Table 2). For EC QPCR compared to DST, there was an 85% threshold-based correlation agreement, a strong correlation (r2=0.88), and false positive and negative rates equivalent to, or less than that of DST (Tables 3 and 4).

TABLE 2

Comparison of EC QPCR with DST

| | Agreement with existing methods (DST) | QPCR under-reported for method | QPCR over-reported for method |
|---|---|---|---|
| Kit | 87% | 7% | 5% |
| Bead beating | 67% | 5% | 28% |

TABLE 3

Comparison of ENT QPCR with ENTEROLERT ™

| | Agreement with existing methods (ENTEROLERT ™)* | QPCR under-reported for method | QPCR over-reported for method |
|---|---|---|---|
| Kit | 86% | 7% | 7% |
| Bead beating | 92% | 0% | 8% |

TABLE 4

Comparison of ENT QPCR with mEI

| | Agreement with existing methods (mEI)* | QPCR under-reported for method | QPCR over-reported for method |
|---|---|---|---|
| Kit | 83% | 2% | 15% |
| Bead beating | 79% | 0% | 21% |

*mEI and ENTEROLERT ™ showed 85% agreement

That which is claimed:

1. A composition for the detection of a multiplicity of strains and species of fecal indicator bacteria in an environmental sample, wherein said composition comprises, in the 5' to 3' direction, one of a fluorophore or a quencher molecule, an oligonucleotide probe comprising SEQ ID NO:5 or 7, the other of the fluorophore or quencher molecule, a PCR blocker moiety, and an oligonucleotide comprising SEQ ID NO:1, wherein a portion of the oligonucleotide probe SEQ ID NO:5 or 7 binds to an amplification product of SEQ ID NO:1.

2. A composition for the detection of a multiplicity of strains and species of fecal indicator bacteria in an environmental sample, wherein said composition comprises, in the 5' to 3' direction, one of a fluorophore or a quencher molecule, an oligonucleotide probe comprising SEQ ID NO:6 or 8, the other of the fluorophore or quencher molecule, a PCR blocker moiety, and an oligonucleotide comprising SEQ ID NO:3 wherein a portion of the oligonucleotide probe SEQ ID NO:6 or 8 binds to an amplification product of SEQ ID NO:3.

3. The composition of claim 1, wherein said PCR blocker moiety is hexethylene glycol (HEG).

4. The composition of claim 2, wherein said PCR blocker moiety is hexethylene glycol (HEG).

5. The composition of claim 1 comprising, in the 5' to 3' direction, a fluorophore, an oligonucleotide comprising SEQ ID NO:7, a quencher, a PCR blocker moiety, and an oligonucleotide comprising SEQ ID NO:1.

6. The composition of claim 2 comprising, in the 5' to 3' direction, a fluorophore, an oligonucleotide comprising SEQ ID NO:8, a quencher, a PCR blocker moiety, and an oligonucleotide comprising SEQ ID NO:3.

7. A kit for the PCR detection of a multiplicity of strains and species of fecal indicator bacteria in an environmental sample comprising the composition of claim 1 and an oligonucleotide comprising SEQ ID NO:2.

8. A kit for the PCR detection of a multiplicity of strains and species of fecal indicator bacteria in an environmental sample comprising the composition of claim 2 and an oligonucleotide comprising SEQ ID NO:4.

9. A kit for the PCR detection of a multiplicity of strains and species of fecal indicator bacteria in an environmental sample comprising the composition of claim 1.

10. A kit for the PCR detection of a multiplicity of strains and species of fecal indicator bacteria in an environmental sample comprising the composition of claim 2.

11. A method for detecting the presence of a multiplicity of strains and species of fecal indicator bacteria in an environmental sample using polymerase-based amplification of a target nucleic acid region present in said fecal indicator bacteria, said method comprising:
   a) providing a test environmental sample suspected of containing fecal indicator bacteria;
   b) contacting said environmental sample with at least a first and a second oligonucleotide primer under conditions sufficient to provide polymerase-based nucleic acid amplification products comprising the target region, wherein said at least a first and a second oligonucleotide primer is selected from the group consisting of:
      i) a first oligonucleotide primer comprising SEQ ID NO:1 and a second oligonucleotide primer comprising SEQ ID NO:2; or,
      ii) a first oligonucleotide primer comprising SEQ ID NO:3 and a second oligonucleotide primer comprising SEQ ID NO:4; and,
   c) detecting the amplified products.

12. The method of claim 11, wherein said first oligonucleotide primer comprising SEQ ID NO:1 further comprises a probe covalently attached to the 5' end of the primer, wherein said probe comprises, in the 5' to 3' direction, one of a fluorophore or a quencher molecule, an oligonucleotide probe comprising SEQ ID NO:5 or 7, the other of the fluorophore or the quencher molecule, and a PCR blocker moiety, wherein nucleotides 1-11 of SEQ ID NO:5 or nucleotides 3-13 of SEQ ID NO:7 bind to an amplification product of SEQ ID NO:1 and SEQ ID NO: 2.

13. The method of claim 11, wherein said first oligonucleotide primer comprising SEQ ID NO:3 further comprises a probe covalently attached to the 5' end of the primer, wherein said probe comprises, in the 5' to 3' direction, one of a fluorophore or a quencher molecule, an oligonucleotide probe comprising SEQ ID NO:6 or 8, the other of the fluorophore or the quencher molecule, and a PCR blocker moiety wherein nucleotides 1-21 of SEQ ID NO:5 or nucleotides 5-25 of SEQ ID NO:8 bind to an amplification product of SEQ ID NO:3 and SEQ ID NO:4.

14. The method of claim 11, wherein said method further comprises the step of isolation of bacterial nucleic acid from the sample provided in step (a).

15. The method of claim 14, wherein said method of isolation comprises bead beating.

16. The method of claim 12, wherein said PCR blocker moiety is hexethylene glycol.

17. The method of claim 11, wherein said polymerase-based amplification is quantitative polymerase chain reaction (QPCR).

18. A method for detecting the presence of a multiplicity of strains and species of fecal indicator bacteria in an environmental sample using polymerase-based amplification of a target nucleic acid region present in said fecal indicator bacteria, said method comprising:
   a) providing a test environmental sample suspected of containing fecal indicator bacteria;
   b) contacting said environmental sample with at least a first and a second oligonucleotide primer under conditions sufficient to provide polymerase-based nucleic acid amplification products comprising the target region, wherein said at least a first and a second oligonucleotide primer is selected from the group consisting of:
      i) a first oligonucleotide primer comprising at least 15 nucleotides of SEQ ID NO:1 and a second oligonucleotide primer comprising at least 15 nucleotides of SEQ ID NO:2; or,
      ii) a first oligonucleotide primer comprising at least 15 nucleotides SEQ ID NO:3 and a second oligonucleotide primer comprising at least 15 nucleotides of SEQ ID NO:4; and,
   c) detecting the amplified products.

* * * * *

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 1
gaacaacgaa ctgaactggc                                                 20

<210> SEQ ID NO 2
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 2
gagcattacg ctgcgatgta                                                 20

<210> SEQ ID NO 3
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 3
```

```
gaggaccgaa cccacgta                                              18

<210> SEQ ID NO 4
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 4
cagtgctcta cctccatcat t                                          21

<210> SEQ ID NO 5
<211> LENGTH: 11
<212> TYPE: DNA
<213> ORGANISM: Artificial Sequence
<220> FEATURE:
<223> OTHER INFORMATION: Oligonucleotide probe

<400> SEQUENCE: 5
tcccggcggg a                                                     11

<210> SEQ ID NO 6
<211> LENGTH: 21
<212> TYPE: DNA
<213> ORGANISM: Artificial Sequence
<220> FEATURE:
<223> OTHER INFORMATION: Oligonucleotide probe

<400> SEQUENCE: 6
gctatttcgg agagaaccag c                                          21

<210> SEQ ID NO 7
<211> LENGTH: 15
<212> TYPE: DNA
<213> ORGANISM: Artificial Sequence
<220> FEATURE:
<223> OTHER INFORMATION: Oligonucleotide probe

<400> SEQUENCE: 7
cctcccggcg ggagg                                                 15

<210> SEQ ID NO 8
<211> LENGTH: 29
<212> TYPE: DNA
<213> ORGANISM: Artificial Sequence
<220> FEATURE:
<223> OTHER INFORMATION: Oligonucleotide probe

<400> SEQUENCE: 8
cggcgctatt tcggagagaa ccagcgccg                                  29
```